US00PP22637P2

(12) United States Plant Patent
Smith

(10) Patent No.: US PP22,637 P2
(45) Date of Patent: Apr. 10, 2012

(54) ***CHRYSANTHEMUM* PLANT NAMED 'SYNMAR PINKA'**

(50) Latin Name: *Chrysanthemum×morifolium*
Varietal Denomination: Synmar Pinka

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 28 days.

(21) Appl. No.: 12/925,368

(22) Filed: Oct. 20, 2010

(51) Int. Cl.
*A01H 5/00* (2006.01)

(52) U.S. Cl. ..... Plt./286

(58) Field of Classification Search ..... Plt./286, Plt./297
See application file for complete search history.

*Primary Examiner* — June Hwu
(74) *Attorney, Agent, or Firm* — S. Matthew Edwards

(57) ABSTRACT

A new *Chrysanthemum* plant named 'Synmar Pinka' particularly distinguished by the large, daisy-type flowers with red-purple colored ray florets, dark yellow-green foliage, large plant size with well-rounded habit, and a natural flowering season of about mid-September.

1 Drawing Sheet

Latin name of the genus and species of the plant claimed: *Chrysanthemum×morifolium.*

Varietal denomination: 'Synmar Pinka'.

BACKGROUND OF THE NEW PLANT

The present invention comprises a new *Chrysanthemum,* botanically known as *Chrysanthemum×morifolium,* and hereinafter referred to by the variety name 'Synmar Pinka'.

'Synmar Pinka' is a product of a planned breeding program. The new cultivar has large, daisy-type flowers with red-purple colored ray florets, dark yellow-green foliage, large plant size with well-rounded habit, and a natural flowering season of about mid-September.

'Synmar Pinka' originated from a hybridization made in February 2006 in a controlled breeding environment in Amanecer, Columbia. The female parent was the unpatented, proprietary plant designated '02-M101'. '02-M101' has duplex/decorative inflorescences, red floret color, and has a 3 week later natural flowering response.

The male parent of 'Synmar Pinka' was the unpatented, proprietary plant designated '00-M401'. '00-M401' has duplex/decorative inflorescences, coral floret color, and a 1 week later natural flowering season. The resultant seed was sown in June 2006 in Alva, Fla.

'Synmar Pinka' was selected as one flowering plant within the progeny of the stated cross in November 2006 in a controlled environment in Alva, Fla.

The first act of asexual reproduction of 'Synmar Pinka' was accomplished when vegetative cuttings were propagated from the initial selection in December 2006 in a controlled environment in Alva, Fla.

BRIEF SUMMARY OF INVENTION

Horticultural examination of plants grown from cuttings of the plant initiated in December 2006, and continuing thereafter, has demonstrated that the combination of characteristics as herein disclosed for 'Synmar Pinka' are firmly fixed and are retained through successive generations of asexual reproduction.

'Synmar Pinka' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6771). 'Synmar Pinka' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Synmar Pinka' with colors being as true as possible with an illustration of this type. The photographic drawing shows a flowering potted plant of the new variety, and a close-up of the flowers.

DETAILED BOTANICAL DESCRIPTION

The plant descriptions and measurements were taken in Gilroy, Calif. in August 2009 under natural light. These plants were about 10 weeks old. The aforementioned photographs were taken in Gilroy, Calif. in late October 2009 outdoors. These plants were approximately 12 weeks of age.

Color references are made to The Royal Horticultural Society Colour Chart (R.H.S.) 2001.

TABLE 1

DIFFERENCES BETWEEN THE NEW VARIETY 'SYNMAR PINKA' AND A SIMILAR VARIETY: 'YOCECILIA' (U.S. Plant Pat. No. 13,798)

| | 'Synmar Pinka' | 'Yocecilia'(U.S. Plant Pat. No. 13,798) |
|---|---|---|
| Flower count and size: | More and larger | Less and smaller |
| Flower color: | Darker | Lighter |
| Ray petal count: | Fewer | More |

Plant:

*Form, growth and habit.*—Herbaceous daisy, garden-type; stems upright and outwardly spreading, freely branching, strong and moderately vigorous growth habit.

*Plant height.*—22-24 cm.

*Plant height* (*inflorescence included*).—25-28 cm.

*Plant width.*—27-30 cm.

*Garden performance and tolerance to weather.*—Very good.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate, simple.

*Immature, leaf color, upper surface.*—Closest to RHS 147A.

*Lower surface.*—Closest to RHS 147B.

*Mature, leaf color, upper surface.*—Closest to RHS 147A, but slightly lighter than the immature color.

*Lower surface.*—Closet to RHS 147B.

*Length.*—5.0-5.6 cm.

*Width.*—3.9-4.5 cm.

*Shape.*—Slightly ovate.

*Base shape.*—Attenuate.

*Apex shape.*—Mucronulate.

*Margin.*—Palmately; irregularly lobed; sometimes irregularly serrate.

*Texture, upper surface.*—Bifid T-shaped hairs.

*Lower surface.*—Bifid T-shaped hairs.

*Color of veins, upper surface.*—Slightly lighter than RHS 147A.

*Color of veins, lower surface.*—Slightly lighter than RHS 147B.

*Petiole color.*—RHS 147B with RHS 147A margins.

*Length.*—2.0-2.3 cm.

*Diameter.*—0.2 cm.

*Texture.*—Bifid T-shaped hairs.

Stem:

*Quantity of main branches per plant.*—About 20.

*Color of stem.*—Closest to RHS 147B but appears lighter with heavy amount of hairs.

*Length of stem.*—12-15 cm.

*Diameter.*—0.3-0.4 cm.

*Length of internodes.*—1.0-4.0 cm.

*Texture.*—Bifid T-shaped hairs.

*Color of peduncle.*—Little lighter than RHS 147B.

*Length of peduncle.*—7.0-10.3 cm.

*Peduncle diameter.*—0.2 cm.

*Texture.*—Heavily covered with Bifid T-shaped hairs.

Inflorescence:

*Type.*—Compositate type, solitary inflorescences (decorative-type) borne terminally above foliage, ray florets arranged acropetally on a capitulum.

*Natural flowering season.*—Mid-September.

*Quantity of inflorescences per plant.*—60 open inforescences and 100-130 buds.

*Lastingness of individual blooms on the plant.*—About 4 weeks.

*Fragrance.*—Slightly spicy.

Bud (just when opening/showing color):

*Color.*—RHS 70A.

*Length.*—1.3-1.7 cm.

*Width.*—1.0-1.2 cm.

*Shape.*—Oblate.

Immature inflorescence:

*Diameter.*—4.0 cm.

*Color of ray florets, upper surface.*—RHS 71C.

*Lower surface.*—RHS 70B with slight striations of RHS 70A.

Mature inflorescence:

*Diameter.*—6.0 cm.

*Depth.*—2.0 cm.

*Total diameter of 'disc'.*—1.0-1.3 cm when fully matured.

*Receptacle height.*—0.5 cm.

*Receptacle diameter.*—1.0 cm.

Ray florets:

*Quantity of florets.*—26-42 in several whorls.

*Color of florets, upper surface.*—*RHS* 70B ground color, with slight striations of RHS 71 B; fading to RHS 77D ground color with good overlay of RHS 70B.

*Lower surface.*—RHS 77B ground color with an overlay of RHS 70B.

*Length.*—2.8-3.1 cm.

*Width.*—0.6-0.7 cm.

*Shape.*—Oblong.

*Apex shape.*—Obtuse to slightly emarginate.

*Margin.*—Entire.

*Texture, upper surface.*—Papillose.

*Lower surface.*—Papillose.

Disc florets:

*Average quantity of florets.*—60-80.

*Color of florets.*—RHS 13B with RHS 1D basally and RHS 1B at the apex.

*Length.*—0.3-0.35 cm.

*Width.*—0.1 cm.

*Shape.*—Tubular, elongated.

*Apex shape.*—Acute, 5 pointed.

Phyllaries:

*Quantity.*—About 20.

*Color, upper surface.*—About RHS 143 C.

*Lower surface.*—RHS 143B to RHS 143C.

*Length.*—0.7-0.8 cm.

*Width.*—0.2-0.3 cm.

*Shape.*—Ovate.

*Apex shape.*—Acute.

*Based.*—Fused.

*Margins.*—Entire.

*Texture, upper surface.*—Glabrous.

*Lower surface.*—Bifid T-shaped hairs.

Reproductive organs:

*Pistil.*1.

*Found on both forets.*—Yes.

*Length.*—0.2-0.3 cm.

*Style color.*—RHS 1C but translucent.

*Style length.*—0.2 cm.

*Stigma color.*—RHS 2B.

*Stigma shape.*—Bi-parted.

*Ovary color.*—RHS 155C.

*Stamens.*—1.

*Found on disc florets only.*—Yes.

*Color of filaments.*—RHS 1C.

*Length filaments.*—0.2-0.25 cm.

*Anther color.*—RHS 12C.

*Anther length.*—0.15 cm.
*Anther shape.*—Oblong.
*Color of pollen.*—RHS 5B.
*Pollen amount.*—Good.
*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Synmar Pinka' substantially as illustrated and described herein.

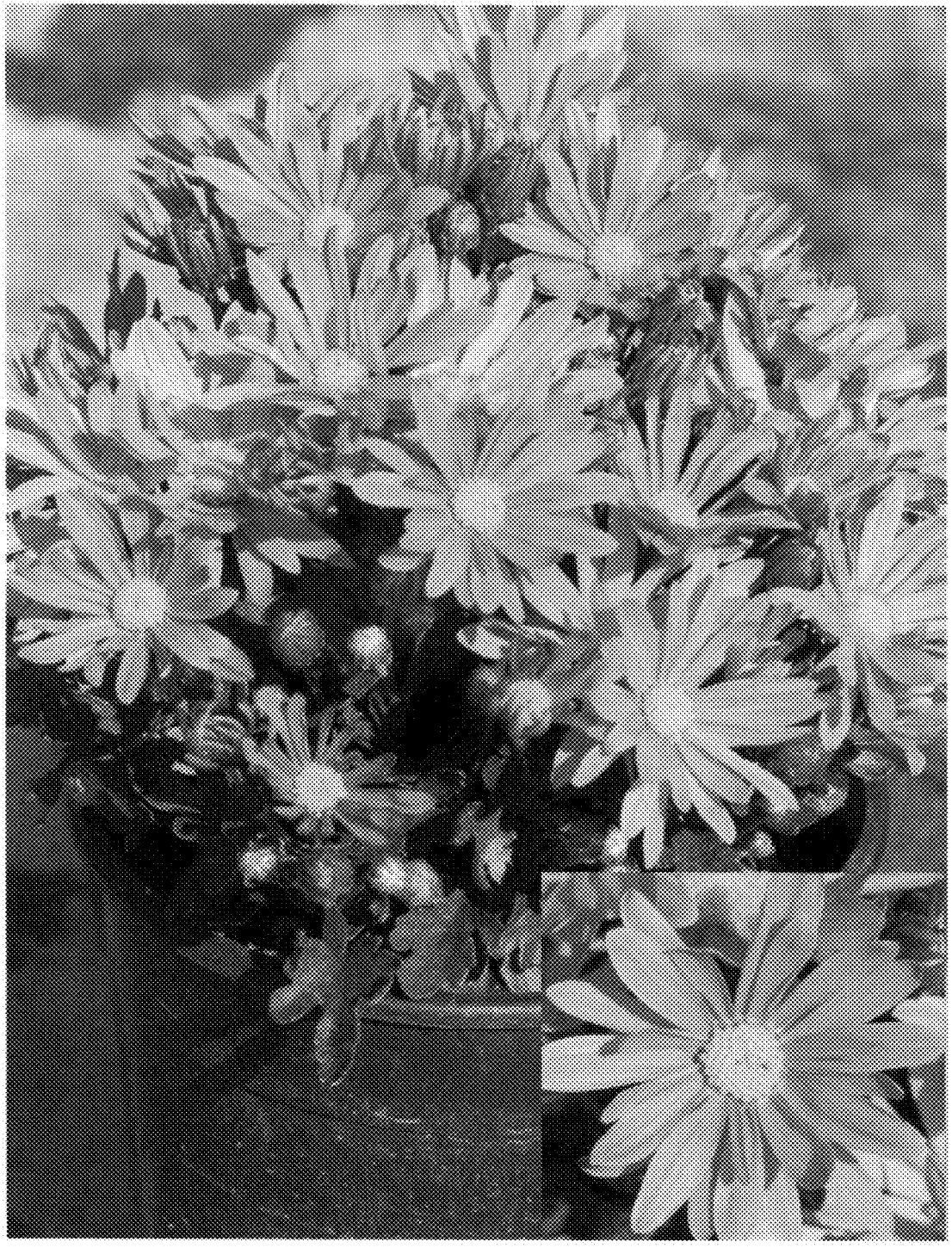

* * * * *